United States Patent [19]
Cornell

[11] 4,152,270
[45] May 1, 1979

[54] PHASE SEPARATION DEVICE

[75] Inventor: William D. Cornell, Ballwin, Mo.

[73] Assignee: Sherwood Medical Industries Inc., St. Louis, Mo.

[21] Appl. No.: 812,533

[22] Filed: Jul. 1, 1977

Related U.S. Application Data

[63] Continuation of Ser. No. 683,867, May 6, 1976, abandoned.

[51] Int. Cl.² .................................................. B01D 21/00
[52] U.S. Cl. ....................... 210/516; 210/518; 210/DIG. 23; 233/1 R; 233/26
[58] Field of Search ............. 210/83, 84, 359, 456, 210/514–518, DIG. 23, DIG. 24; 233/1 A, 1 R, 26; 23/230 B, 258.5, 259, 292; 128/214 R

[56] References Cited

U.S. PATENT DOCUMENTS

| | | | |
|---|---|---|---|
| 3,508,653 | 4/1970 | Coleman | 210/83 |
| 3,741,400 | 6/1973 | Dick | 210/516 |
| 3,814,258 | 6/1974 | Ayres | 210/359 |
| 3,832,141 | 8/1974 | Haldopoulos | 23/259 |
| 3,846,077 | 11/1974 | Ohringer | 23/259 |
| 3,862,042 | 1/1975 | Ayres | 210/516 |
| 3,897,337 | 7/1975 | Ayres | 210/136 |
| 3,897,340 | 7/1975 | Ayres | 210/314 |
| 3,897,343 | 7/1975 | Ayres | 210/516 |
| 3,935,113 | 1/1976 | Ayres | 210/516 |
| 3,945,928 | 3/1976 | Ayres | 210/516 |

*Primary Examiner*—Frank Sever
*Attorney, Agent, or Firm*—Stanley N. Garber; William R. O'Meara

[57] ABSTRACT

A fluid collection device for receiving a liquid, such as blood, and which is adapted to be centrifuged to separate it into its relatively light and heavy phases. The collection device has a phase partitioning device having a specific gravity intermediate those of the light and heavy phases of the blood so that it automatically moves during centrifugation to substantially the interface of the phases to sealingly partition them from each other. The device has a resilient sealing member which is of conical or "umbrella" configuration, and another member of different specific gravity connected to the sealing member and having stabilizing members for maintaining the sealing member properly oriented in the container. The sealing member partially collapses during centrifugation to allow blood components to pass by the sealing member. As the phases become separated and the centrifugal forces decrease, the sealing member expands radially outwardly and sealingly engages the walls of the container providing a barrier between the light and heavy phases upon complete phase separation.

20 Claims, 8 Drawing Figures

PHASE SEPARATION DEVICE

This is a continuation of application Ser. No. 683,867, filed May 6, 1976, now abandoned.

BACKGROUND OF THE INVENTION

This invention relates to fluid collection devices and more particularly to liquid collection devices having means for partitioning separated lighter and heavier phases of the liquid.

In the testing of blood samples, for example, whole blood is usually drawn into an evacuated collection tube and then the tube is placed in a centrifuge for separating the lighter phase, serum or plasma, and the heavier or cellular phase so that the individual phases may be isolated and tested. Many different types of phase partitioning devices which provide a barrier or seal between the separated phases have been used or proposed for the purpose of allowing the lighter phase to be decanted or poured into a transfer tube free of cells or to enable the two phases to remain in the collection tube without intermixing during shipment to a laboratory where the lighter phase is removed and subjected to analysis.

With some phase separation or partitioning devices, the stopper of the sampling tube, after the light and heavy phases have been separated in a centrifuge, is removed and the light phase is drawn or siphoned off. In some cases, a barrier member is inserted into the tube that allows the light phase to pass by it and which is stopped at the interface of the two phases to provide a seal between the phases. These methods require the opening of the sampling tube after the phases are separated with the possibility of causing them to be intermixed. Also, it is time consuming and subjects the personnel to the possibility of coming in contact with a virus or the like, such as hepatitis.

Other types of separation devices have been used such as disclosed in U.S. Pat. No. 3,852,194 wherein a gel, such as silicone gel, is disposed in the tube. The gel has a specific gravity intermediate the light and heavy phases so that during centrifugation, it automatically moves to the interface of the separated phases to provide a seal. One disadvantage of this type of partitioning system is that the gel may affect the liquid. For example, silicone oil may enter the light phase and cause clogging in the serum or plasma testing equipment. In U.S. Pat. No. 3,814,248, a spool and ball partitioning device is disclosed. One of the problems of this device is that there are two different seals required, one between the spool and the wall of the tube, and the other between the ball and the spool, and this increases the danger of cells passing into the lighter phase to contaminate it. In U.S. Pat. No. 3,508,653, a deformable piston member having a specific gravity intermediate those of the separated phases is attached to the stopper and after centrifugal separation of the phases, the centrifuge is speeded up to cause the piston to separate from the stopper and move to the interface. One of the disadvantages of the latter type of device is that the centrifuge must be controlled to operate at two different speeds.

SUMMARY OF THE INVENTION

Accordingly, an object of the present invention is to provide a novel partitioning means for maintaining the lighter and heavier phases of a fluid, such as blood, separated and which is highly effective, relatively simple and economical. In accordance with the present invention, a phase separation device is disposed within a container for receiving fluid which is separable into lighter and heavier phases. The phase separation device has a specific gravity intermediate the specific gravities of the lighter and heavier phases so that during centrifugation, the device moves substantially to the interface to provide a seal. The device includes a resilient portion having a generally conical or umbrella configuration which resiliently engages the inner wall of the container to provide a seal between the phases. These, as well as other objects and advantages of the present invention will become apparent from the following detailed description and drawings.

DESCRIPTION OF THE PREFERRED EMBODIMENTS

Figure 1:
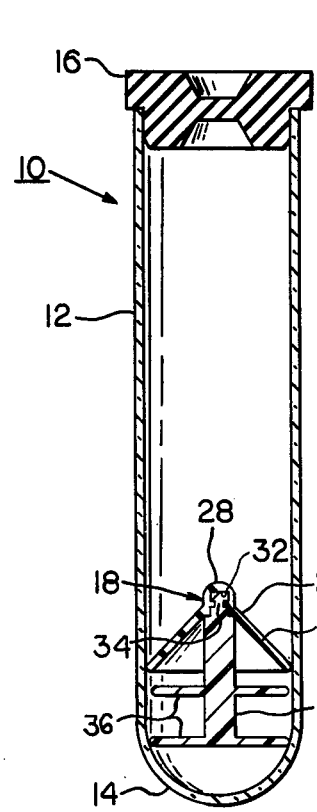
FIG. 1 is an elevational cross-sectional view of a blood collection tube containing a phase partitioning device in accordance with a preferred embodiment of the present invention.
Figure 2:
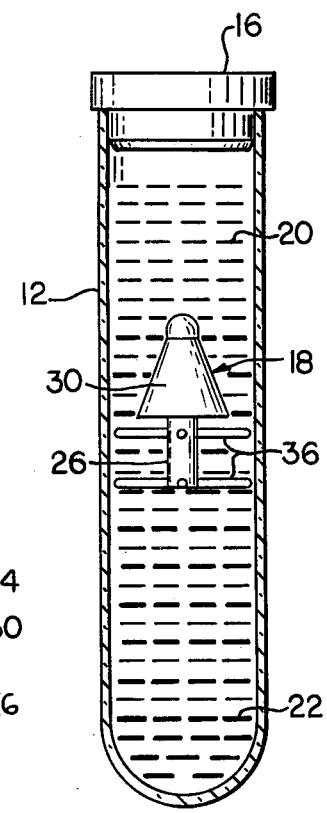
FIG. 2 is an elevational cross-sectional view of the collection tube of FIG. 1 after blood has been drawn into the tube and during an intermediate stage in the centrifugation of the blood.
Figure 3:
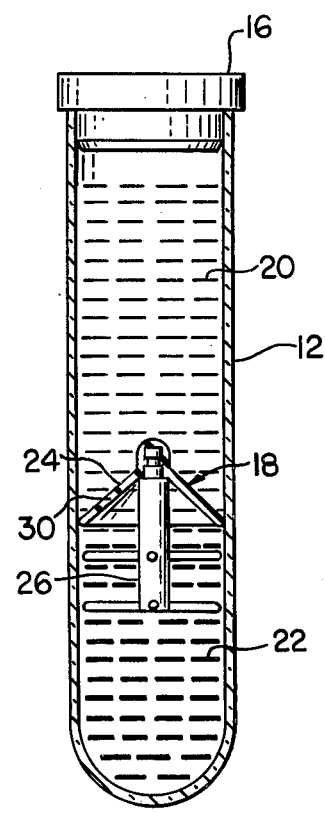
FIG. 3 is an elevational cross-sectional view similar to FIG. 2 but after complete separation of the phases and centrifugation.

Referring now to the drawing, and especially to FIGS. 1-3, there is shown a fluid collection device 10 including a container or blood collection tube 12 which is preferably of transparent glass and which is shown closed at the bottom by an integral portion 14 of the tube. The tube has an upper open end that is closed by a closure or stopper 16 which extends into the open end in sealing engagement with the inner side walls of the tube. The stopper 16 is pierceable by a needle and self-sealing after being pierced. The stopper may be formed of a suitable rubber, for example, an elastomer such as butyl rubber. The collection tube is provided with a desired negative or partial vacuum that is maintained by the stopper 16. Disposed within tube 12 is a movable blood phase partitioning or separation device 18.

A sample of blood may be drawn into the blood collection device 10 by use of a double-ended needle cannula or a conventional needle holder and tube guide device (not shown) having a double-ended needle cannula. For example, after the distal pointed end of the needle cannula is inserted into the vein of a patient, the device 10 is moved within the holder until the proximal pointed end of the needle cannula has pierced the stopper 16 and communicates with the interior of the tube 12, whereupon blood flows into the tube. The filled tube is removed from the holder and placed in a centrifuge with the lower end 14 radially outwardly of the stopper and axis of rotation of the centrifuge.

As will be more fully explained hereinafter, the phase partitioning device 18 is constructed so that it has a specific gravity intermediate those of the separated light and heavy phases indicated at 20 and 22, respectively, in FIGS. 2 and 3, so that it moves during centrifugation substantially to the interface between the two phases, and provides a seal automatically upon completion of the centrifugation of the blood.

The phase partitioning device 18 includes an upper portion or member 24, and a lower portion or member 26 attached to the upper member 24. The upper member 24 is formed of a resilient elastomeric material such as rubber or synthetic rubber or plastic, and is formed or molded to have a normal conical or "umbrella" configuration. Member 24 has a vertex 20 at the top which is integral with a downwardly inclined, conical skirt 30. The vertex is at the longitudinal or vertical axis of the member. The bottom side of the vertex has a recess 32 having an undercut to receive the upper notched end 34 of the lower member 26 to secure the members 24 and 26 together. The lower member 26 may be formed of a relatively rigid or hard material such as a suitable plastic, for example, polypropylene. The member 26 is shown provided with eight, integrally formed, radial stabilizing rods 36 which maintain the partitioning device 18 in an upright or proper orientation during centrifugation. The rods 36 are arranged to provide upper and lower sets of four, with the rods in each set disposed 90° apart. Various other forms of stabilizing members are, of course, possible.

The outer periphery of the lower extremity of the skirt 30 has a diameter slightly larger than the inside diameter of tube 12 when in its normal or manufactured condition, substantially the condition shown in FIG. 1. As seen in FIG. 1, it is in slight frictional engagement with the inside wall of the tube near the lower end 14.

The materials used in forming the upper portion 24 and the lower portion 26 of partitioning device 18 are chosen such that the total or average specific gravity, that is, both of the members together, is intermediate the specific gravities of the separated lighter and heavier phases 20 and 22. For example, the combination of materials may be chosen such that the specific gravity of the device 18 is 1.045 since the light phase is generally about 1.03, and the heavier cellular phase 22 is generally about 1.08. Also, the lower member 26 is made to have a specific gravity less than that of the heavier phase 22 and that of the upper member 24 while the upper member is made to have a specific gravity greater than that of the lighter phase 20.

The partitioning device 18 is inserted into the empty sampling tube 12, for example, during manufacture, with the upper conical member 24 of gravity specific gravity on top or closer to the stopper 16 than the lower member 26 of less specific gravity so that the member 24 will be radially inward of member 26 and tube end 14 during centrifugation. During centrifugation, the member 26 tends to move upwardly, as viewed in the drawings, and the member 24 downwardly so that the umbrella-shaped upper member 24 moves radially inwardly about the upper end 34 of member 26 and allows the blood components to move past the device. As seen in FIG. 2, the skirt 30, during centrifugation, is partially collapsed toward the longitudinal or vertical axis of device 18 and the device moves up toward the lighter phase 20 since the device has an intermediate specific gravity. In FIG. 3, the device 10 is shown after complete separation of the phases and after the centrifuge has slowed down or stopped. The conical or umbrella portion 30 is shown expanded outwardly toward its normal or unstressed conical shape with its periphery in resilient, frictional engagement with the inner walls of the tube substantially at or slightly above the interface of the light and heavy phases 20 and 22 to provide a permanent partition or seal between the two phases. The specific gravity of the device is preferably chosen such that the upper member 24, as it expands into sealing engagement with the tube 12, is fully above the heavier phase 22 so that it does not trap or carry any cells into the lighter phase 20 above the device 18 to avoid contamination of the ligher phase. After complete centrifugation, such as indicated in FIG. 3, the tube 12 may be stored or otherwise shipped or mailed to a laboratory for blood analysis, such as the testing of the serum or plasma phase. During storage or mailing, the partitioning device 18 prevents cells from the lower phase 22 from entering and contaminating the lighter phase 20.

Figure 4:
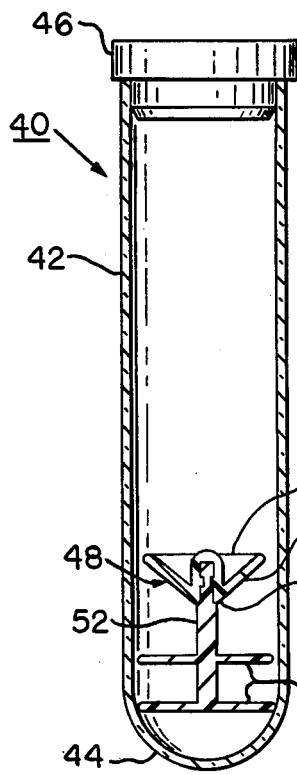
FIG. 4 is an elevational cross-sectional view of a blood collection tube containing a phase partitioning device of modified form.
Figure 5:
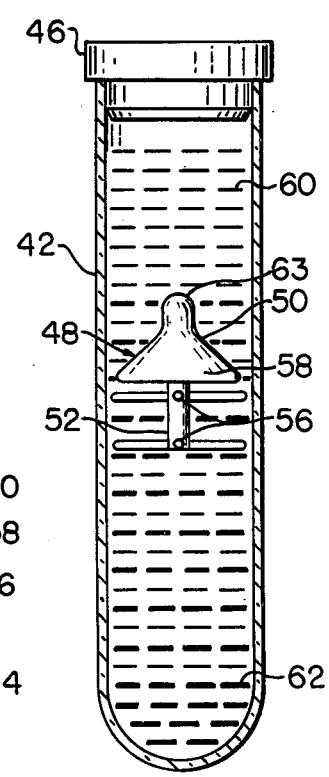
FIG. 5 is an elevational cross-sectional view of the collection tube of FIG. 4 after it is filled with blood and during a stage in the centrifugation of the blood.
Figure 6:
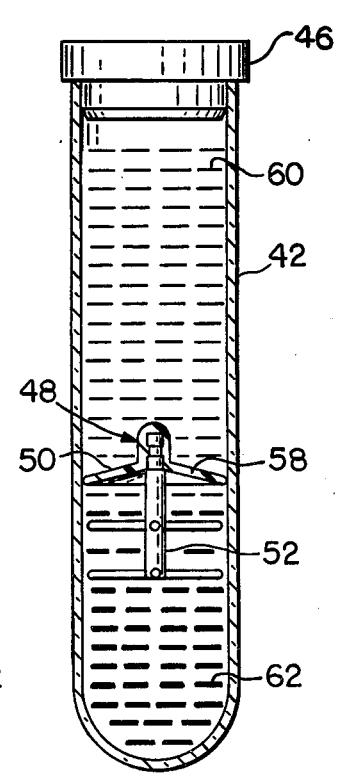
FIG. 6 is an elevational cross-sectional view of the blood collection tube of FIG. 1 after complete centrifugation of the blood.

In FIGS. 4–6, there is shown a blood collection device 40 in accordance with a modified embodiment which include a blood sampling tube 42 having an integrally closed lower end 44 and an upper open end closed by a rubber stopper 46. Disposed within the tube 42 is a blood phase partitioning or separating device 48 of modified construction. The phase partitioning device 48 includes an upper portion or member 50 having a conical or "umbrella" configuration, and a lower portion or member 52 having eight stabilizing, radially outwardly extending rods 54. The upper member 50 is formed of an elastomeric material such as butyl rubber or the like, and the lower member 52 is preferably formed of a relatively hard plastic such as polypropylene or the like. In this case, the upper umbrella-shaped member 50 has an inverted umbrella configuration in its normal manufactured state, that is, it has a vertex 56 and a skirt 58 which is inclined upwardly toward the stopper 46 and radially outwardly from the vertex in the normal or unstressed condition of the member as seen in FIG. 4. The outer diameter of the skirt 58 is maximum at its upper end and is substatially less than the inner diameter of sampling tube 42 when the member 50 is in its normal condition. The phase separating device 48 is also formed of materials such that it has a specific gravity intermediate the specivic gravities of the separated phases, which phases are illustrated at 60 and 62 in FIGS. 5 and 6. Also, the upper elastomeric member 50 has a specific gravity greater than that of the lighter phase 60 and the lower member 52, while member 52 has a specific gravity less than that of the heavy phase 62. During centrifugation, there is an upward force at the vertex 56 and a downward force acting on the periphery of the member 50 due to the differences in specific gravities of the upper and lower members. Also, the outer maximum diameter of skirt 58 is such that during centrifugation of the sampling tube, and after whole blood is introduced into it through stopper 46, the skirt is able to reverse or invert itself to the condition illustrated in FIG. 5 where an intermediate stage in the centrifugation is indicated. The skirt 58, as seen in FIG. 5, is now inclined downwardly and radially outwardly and has an upper vertex 63 at the vertical axis of the member 50.

After complete separation of the two phases 60 and 62, the centrifuge is turned off and the skirt 58 of the partitioning device 48 moves radially outwardly and upwardly into tight frictional engagement with the inner walls of the tube 42 adjacent the interface of the separated phases, as shown in FIG. 6. The material and outer diameter of the upper member 50 are chosen such that, while the umbrella portion 58 can invert under centrifugal forces, it cannot return to its original inverted or normal condition (FIG. 4) as the centrifugal forces decrease since it engages the inner wall of the tube 42. In this way, a substantial force is exerted by the resilient upper member 50 to provide a good seal between the two blood phases.

Figure 7:
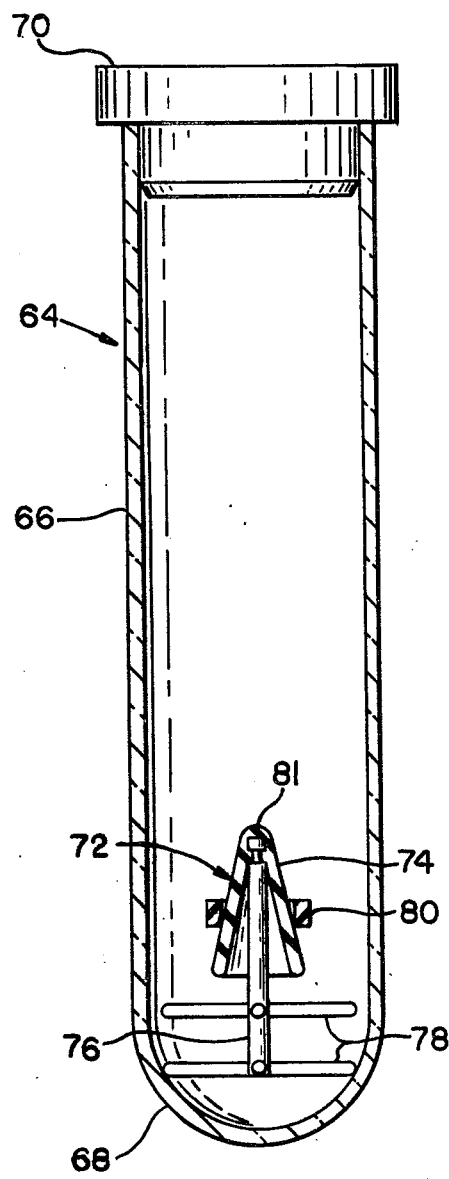
FIG. 7 is an elevational cross-sectional view of a collection tube in accordance with a further modified embodiment of the invention.
Figure 8:
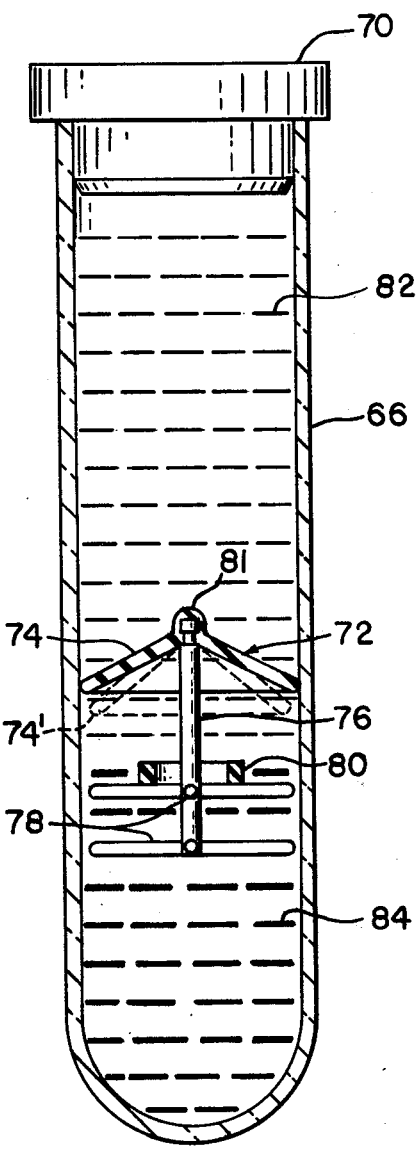
FIG. 8 is an elevational cross-sectional view of the collection tube of FIG. 7 but after complete centrifugation and blood phase separation.

FIGS. 7 and 8 illustrate a fluid collection device indicated generally at 64 in accordance with another modified embodiment of the present invention. Device 64 is shown including a blood sampling tube 66 closed at the lower end by an integral portion 68 and having a resilient, pierceable stopper 70 closing the upper end of the tube. Disposed within the sampling tube is a blood phase or partitioning device indicated generally at 72 which has a specific gravity intermediate that of the separated phases. The partitioning device 72 includes a resilient, elastomeric umbrella or conically-shaped upper member 74, a relatively rigid, lower member 76 having radial stabilizing bars or rods 78, and a holding ring 80. The member 74 has a vertex 81 at the top which faces the stopper 70. In this illustrated embodiment, the umbrella-shaped member 74, in its normal unstressed condition, extends downwardly and radially outwardly, and has a maximum outer peripheral diameter slightly greater than the inner diameter of tube 66 and, in general, a configuration substantially as shown in FIG. 8. In the unactuated condition, before centrifugation, the upper member 74 is held in a partially collapsed condition, as shown in FIG. 7, by the ring 80 surrounding the member 74. The ring has a diameter substantially less than the diameter of the outer periphery of the umbrella-shaped member 74 when it is in its unrestricted or normal condition to thereby maintain the umbrella-shaped member "closed" or partially collapsed as in FIG. 7. The average specific gravity of the three members 74, 76 and 80 together must be intermediate the specific gravities of the light and heavy phases, indicated at 82 and 84, in order to arrive at or near the interface of the two phases after centrifugation. The specific gravity of the lower member 76 is less than that of the upper member 74, and the specific gravity of the ring 80 is greater than the average of the two members 74 and 76. During centrifugation, the ring slides down and off of the member 74 and since the lower member 76 has a specific gravity less than that of the upper member 74, the centrifugal forces tend to maintain the upper member partially collapsed to allow liquid to pass by it until complete separation. For example, 74′ in FIG. 8 illustrates an intermediate position of the upper member 74 during centrifugation but before complete separation of the phases. In other words, the upper member 74 will be partially collapsed even after the ring has moved off the member. In FIG. 8, the device 64 is shown after complete phase separation and centrifugation and it is seen that the upper member 74 is in sealing engagement with the tube 66.

In each of the illustrated embodiments, the upper elastomeric member has a specific gravity greater than that of the lower plastic member so that the centrifugal forces produce a force upwardly against the vertex of the upper member while the upper member tends to move downwardly and inwardly toward the axis, that is, tends to collapse about the vertex due to centrifugal forces. It will be apparent that various combinations of materials may be used so as to produce a specific gravity difference between the upper and lower members and such that the total or average specific gravity of the entire device is intermediate the two phases of blood. For example, the upper member, which has a specific gravity greater than that of the lighter phase, may have a specific gravity greater than that of the heavy phase, and the lower member which lighter than the heavy phase, may has a specific gravity less than that of the light phase. On the other hand, both members in some cases, depending on the materials used, may be both of specific gravities intermediate the upper and lower phases but with the lower member having a specific gravity less than that of the upper member to allow collapsing of the member during centrifugation.

Preferably, during manufacture, the partitioning device is placed in the tube and then the stopper inserted while in a negative atmosphere. It may be desirable in some cases to employ a tube which is open at both ends and then to close each end with a stopper. Where the configuration of the partitioning device is such that it may not allow a clot to pass by it, the above double-stopper tube can be advantageously used, since whole blood can be introduced below the partitioning device.

As various changes could be made in the above constructions without departing from the scope of the invention, it is intended that all matter contained in the above description or shown in the accompanying drawings shall be interpreted as illustrative and not in a limiting sense.

What is claimed is:

1. A fluid collection device for receiving a sample of liquid centrifugally separable into relatively light and heavy phases comprising a closed container, and centrifugally actuated phase partitioning means movable in said container and having a specific gravity intermediate the specific gravities of the phases, said partitioning means including a first member of resilient elastomeric material having a normal generally conical configuration when in said container and a specific gravity greater than that of the light phase, and a second member connected to said first member and having a specific gravity less than that of said first member so that during centrifugation of the collection device the difference between the specific gravities of said members causes partial collapse of said first member to allow liquid to flow past said partitioning means, said partitioning means being movable during centrifugation of the collection device due to the specific gravity thereof such that said first member is movable substantially to the interface of the two phases to provide a liquid impervious partition therebetween after centrifugation.

2. The device of claim 1 wherein said first member has a vertex at the longitudinal axis of said partitioning means, and said second member is connected to said first member at said vertex so that during centrifugation the outer periphery of said first member moves toward said axis, and after centrifugation, sealingly engages the inner wall of said container substantially at the interface of the separated phases.

3. The device of claim 2 wherein said second member includes means extending generally radially outwardly from the longitudinal axis of said partitioning means to maintain said partitioning means in a desired orientation relative to said container.

4. The device of claim 2 wherein said first member normally has an inverted umbrella configuration with walls inclined radially outwardly toward one end of said container and changes during centrifugation to a second umbrella configuration wherein said walls are inclined radially outwardly toward the opposite end of said container.

5. The device of claim 4 wherein the walls of said first member are movable, while said first member is in said second umbrella configuration, into sealing engagement with the inner walls of said container.

6. The device of claim 4 wherein said second member includes means extending generally radially outwardly from the longitudinal axis of said partitioning means to maintain said device in a desired orientation in said container.

7. A blood collection device for receiving whole blood and adapted to be centrifuged to separate the lighter phase from the heavier cellular phase comprising a tube, means closing one end of said tube, a pierceable stopper closing the opposite end of said tube, said tube having a negative pressure therein for drawing blood into the tube by means of a cannula piercing said stopper, and a phase partitioning device movable within said tube including a first member of generally conical configuration having a vertex at the longitudinal axis and a skirt having walls tapering radially outwardly relative to said vertex, said first member being formed of a resilient elastomeric material and having a specific gravity greater than that of the lighter phase, and a second member of substantially rigid material connected to said first member at said vertex, said partitioning device having a specific gravity intermediate the specific gravities of the separated lighter and heavier phases of the blood so that it moves during centrifugation of the collection device to a position adjacent the interface of the separated blood phases, said first member having a specific gravity greater than that of said second member and being predeterminately oriented with said first member disposed between said stopper and said second member so that during centrifugation the difference in specific gravities of said members causes at least a partial collapse of said skirt to permit liquid to flow past said partitioning device between the radially outermost surface thereof and the inner wall of said tube, said skirt after centrifugation sealingly engaging the inner wall of said tube to form a liquid impervious partition between the separated heavier and lighter phases.

8. The device of claim 7 wherein said second member includes stabilizing means for maintaining said device predeterminately oriented during centrifugation.

9. The device of claim 7 wherein said skirt, in its normal unstressed state, has walls inclined radially outwardly toward said one end.

10. The device of claim 7 wherein said skirt in its normal unstressed configuration extends radially outwardly toward said stopper.

11. The device of claim 10 wherein said skirt is capable during centrifugation of everting itself so that it extends radially outwardly toward said one end of said tube.

12. The device of claim 7 wherein said phase partitioning means has a specific gravity such that after complete phase separation said partitioning device is disposed slightly above the interface of the lighter and heavier phases with portions of the lighter phase on each of the axially opposed sides of said skirt.

13. A fluid collection device for receiving a sample of liquid centrifugally separable into relatively light and heavy phases comprising a closed container, and centrifugally actuated phase partitioning means in said container having a specific gravity intermediate the specific gravities of the phases, said partitioning means including a first member of elastomeric material having a normal conical configuration with a vertex at the longitudinal axis of said partitioning means and a specific gravity greater than that of the light phase, a second member connected to said first member at said vertex and having a specific gravity less than that of said first member, and a holding member at least partially encircling said first member to maintain it in a predetermined conical configuration in which it is partially collapsed with the outer periphery thereof spaced from the inner wall of the container so that during centrifugation the liquid is allowed to flow past said partitioning device, said holding member having a specific gravity greater than that of said first and second members together and movable off of said first member in response to centrifugal forces during centrifugation, said partitioning device being movable to a position adjacent the interface of the two phases with said first member resiliently sealingly engaging the inner wall of said container adjacent the interface of the separated phases to provide a partition between the phases after centrifugation.

14. The device of claim 13 wherein said second member has radially outwardly extending means thereon axially spaced from said first member, and said holding means is moveable into a position on said radially outwardly extending means between said first member and said radially outwardly extending means subsequent to movement thereof off of said first member.

15. A blood collection device for receiving whole blood and adapted to be centrifuged to separate the lighter phase from the heavier cellular phase comprising a tube, means closing one end of said tube, a pierceable stopper closing the opposite end of said tube, said tubing having a negative pressure therein for drawing blood into the tube by means of a cannula piercing said stopper, and a phase partitioning device within said tube including a first member of conical configuration having a vertex at the longitudinal axis and a skirt having walls tapering radially outwardly from said vertex, said skirt, in its normal unstressed state, having walls inclined radially outwardly toward said one end, said first member being formed of a resilient elastomeric material, a second member of substantially rigid material connected to said first member at said vertex, and a ring surrounding said skirt to hold said skirt in a partially collapsed condition, said ring having a specific gravity greater than the average of the specific gravities of said first and second members and movable off of said skirt during centrifugation to allow said skirt to move radially outwardly toward engagement with the inner walls of said tube, said partitioning device having a specific gravity intermediate the specific gravities of the separated lighter and heavier phases of the blood, said first member having a specific gravity greater than that of said second member and being predeterminately oriented with said first member disposed between said stopper and said second member.

16. A blood collection device for receiving whole blood and adapted to be centrifuged to separate the blood into its relatively lighter phase and its relatively heavier cellular phase comprising an elongate container, means closing one end of said container, a stopper closing the opposite end of said container, and movable phase partitioning means in said container having a specific gravity intermediate the specific gravity of the separated lighter and heavier phases so that during centrifugation of the device and separation of the phases said partitioning means moves relative to said container and reaches a location adjacent the interface between the separated lighter and heavier phases, said partitioning means including a first resilient member having a radially outer periphery sealingly engageable with the inner wall of said container and having a specific gravity greater than that of the lighter phase, and a second member connected to said first member and disposed between said first member and said one container end, said second member having a specific gravity less than that of said first member so that during centrifugation of the device in a manner such that the blood cells move toward said one container end, said first member changes its configuration due to its connection with said second member and the differences in specific gravities of said members so as to allow the flow of fluid from one side to the other side of said partitioning device during separation of the phases, said first member being in sealing engagement with the inner wall of said container and providing a liquid impervious separating partition between the separated phases subsequent to centrifugation of the device.

17. The device of claim 16 wherein second member is connected to said first member such that at least a portion of the radially outer periphery of said first member moves radially inwardly from the inner wall of the container to allow fluid to move past said partitioning means between the radially outer periphery of said first member and the inner wall of said container during centrifugation of the device, said radially outer periphery of said first member being in resiliently urged sealing contact with the inner wall of said container to provide a partition between the lighter and heavier phases subsequent to the centrifugation of the device.

18. A blood collection device for receiving whole blood and adapted to be centrifuged to separate the blood into its lighter and heavier phases comprising a tube, means closing one end of said tube, a pierceable stopper closing the opposite end of said tube, said tube having a negative pressure therein for drawing blood into the tube by means of a cannula piercing said stopper, and a phase partitioning device movable within said tube including a first member of resilient, elastomeric material having a radially outer periphery resiliently engageable with the inner wall of said tube to prevent the flow of liquid past said partitioning device, and a second member connected to said first member, said partitioning device having a specific gravity intermediate the specific gravities of the separated lighter and heavier phases of the blood so that it moves during centrifugation of the collection device to a position adjacent the interface of the separated blood phases, said first member having a specific gravity greater than that of said second member and the lighter phase, and being predeterminately oriented with said first member disposed between said stopper and said second member so that during centrifugation the difference in specific gravities of said members causes at least a partial collapse of said first member to permit liquid to flow past said partitioning device between said radially outer periphery of said first member and the inner wall of said tube, said radially outer periphery of said first member being movable into sealing engagement with the inner wall of said tube to form a liquid impervious partition between the separated heavier and lighter phases after centrifugation of the collection device.

19. A blood collection device for receiving whole blood and adapted to be centrifuged to separate the lighter phase from the heavier cellular phase comprising a tube, means closing one end of said tube, a pierceable stopper closing the opposite end of said tube, said tube having a negative pressure therein for drawing blood into the tube by means of a cannula piercing said stopper, and a phase partitioning device movable within said tube including a first member of generally conical configuration having a vertex at the longitudinal axis and a skirt having walls tapering radially outward relative to said vertex, said first member being formed of a resilient elastomeric material and having a specific gravity greater than that of the lighter phase, a second member of substantially rigid material connected to said first member at said vertex, said partitioning device having a specific gravity intermediate the specific gravities of the separated lighter and heavier phases of the blood so that it moves during centrifugation of the collection device to a position adjacent the interface of the separated blood phases, said first member having a specific gravity greater than that of said second member and being predeterminately oriented with said first member disposed between said stopper and said second member so that during centrifugation the difference in specific gravities of said members causes at least a partial collapse of said skirt to permit liquid to flow past said partitioning device between the radially outermost surface thereof and the inner wall of said tube, said skirt after centrifugation sealingly engaging the inner wall of said tube to form a liquid impervious partition between the separated heavier and lighter phases, and centrifugally actuated holding means holding said skirt in a partially collapsed configuration so that fluid can pass said partitioning device during phase separation, said holding means being moveable and having a specific gravity relative to that of said first and second members together such that said holding means moves to free said skirt during centrifugation of the collection device to allow said skirt to subsequently sealingly engage the inner wall of said container.

20. A blood collection device for receiving whole blood and adapted to be centrifuged to separate the lighter phase from the heavier cellular phase comprising a tube, means closing one end of said tube, a pierceable stopper closing the opposite end of said tube, said tube having a negative pressure therein for drawing blood into the tube by means of a cannula piercing said stopper, and a phase partitioning device movable within said tube including a first member of generally conical configuration having a vertex at the longitudinal axis and a skirt having walls tapering radially outward relative to said vertex, said first member being formed of a resilient elastomeric material, a second member of substantially rigid material connected to said first member at said vertex, said partitioning device having a specific gravity intermediate the specific gravities of the separated lighter and heavier phases of the blood so that it moves during centrifugation of the collection device to a position adjacent the interface of the separated blood phases, said second member including radially outwardly extending stabilizing means for maintaining said first member predeterminately oriented during said centrifugation, said first member having a specific gravity greater than that of said second member and being predeterminately oriented with said first member disposed between said stopper and said second member so that during centrifugation the difference in specific gravities of said members causes at least a partial collapse of said skirt to permit liquid to flow past said partitioning device between the radially outermost surface thereof and the inner wall of said tube, said skirt after centrifugation sealingly engaging the inner wall of said tube to form a liquid impervious partition between the separated heavier and lighter phases, and centrifugally actuated holding means holding said skirt in a partially collapsed configuration so that fluid can pass said partitioning device during phase separation, said holding means being moveable and having a specific gravity relative to that of said first and second members together such that said holding means moves to free said skirt during centrifugation of the collection device to allow said skirt to subsequently sealingly engage the inner wall of said container, said holding means being moveable to a position on said second member between said first member and said stabilizing means after moving to free said skirt.

* * * * *